US007133129B2

(12) United States Patent
Lee et al.

(10) Patent No.: US 7,133,129 B2
(45) Date of Patent: Nov. 7, 2006

(54) CARGO INSPECTION APPARATUS HAVING A NANOPARTICLE FILM AND METHOD OF USE THEREOF

(75) Inventors: Yuan-Hsiang Lee, Winchester, MA (US); William Joseph McGann, Raynham, MA (US); Kenneth Arthur Ribeiro, North Reading, MA (US); Tao Deng, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 277 days.

(21) Appl. No.: 10/901,823

(22) Filed: Jul. 29, 2004

(65) Prior Publication Data

US 2006/0023209 A1   Feb. 2, 2006

Related U.S. Application Data

(63) Continuation-in-part of application No. 10/843,832, filed on May 12, 2004.

(51) Int. Cl.
*G01J 3/44* (2006.01)
*G01N 21/65* (2006.01)

(52) U.S. Cl. .................................................... 356/301
(58) Field of Classification Search ................ 356/301
See application file for complete search history.

(56) References Cited

U.S. PATENT DOCUMENTS

| 4,674,878 | A | * | 6/1987 | Vo-Dinh ...................... 356/301 |
| 5,017,007 | A | * | 5/1991 | Milne et al. ................. 356/301 |
| 5,255,067 | A | * | 10/1993 | Carrabba et al. ............ 356/301 |
| 5,621,522 | A | | 4/1997 | Ewing et al. ................ 356/301 |
| 5,642,393 | A | | 6/1997 | Krug et al. ..................... 378/57 |
| 6,610,977 | B1 | | 8/2003 | Megerle ...................... 250/287 |
| 7,046,358 | B1 | * | 5/2006 | Barker et al. ............... 356/301 |

FOREIGN PATENT DOCUMENTS

WO   WO 98/10289   12/1998

OTHER PUBLICATIONS

S. Farquharson, et al., "Trace drug analysis by surface-enhanced Raman spectroscopy;" SPIE 2000; 4200, 89-95.
Steinfeld, et al., "New spectroscopic methods for environmental measurement and monitoring;" SPIE; 1999 3853, 28-33.
Simeonsson, Josef B., "Development of a SERS-Based Sensor for Monitoring Air Quality in Space Cabin Environments;" SAE Technical Paper Series Jul. 7-10, 2003.
Carter, J. Chance et al., "Raman spectroscopy for in Situ Identification of Cocaine and Selected Adulterants;" Applied Spectroscopy 2000; 54(12):1876-1881.
Wang, J. et al., "Fabricating Surface Enhanced Raman Scattering (SERS)-Active Substrates by Assembling Colloidal Au Nanoparticles with Self-Assembled Monolayers;" Jpn. J. Appl. Phys., Oct. 15, 1996; 35:L1381-L1384.

(Continued)

*Primary Examiner*—F. L. Evans
(74) *Attorney, Agent, or Firm*—Eugene Hyun, Esq.

(57) ABSTRACT

A cargo inspection apparatus for the inspection of an analyte carried by a medium is disclosed. The apparatus includes a housing having an inlet allowing for entry of the medium and an outlet allowing for exit of the medium, and an adsorber disposed within the housing in fluid communication with the medium flow from the inlet to the outlet, the adsorber includes a substrate having disposed thereon a nanoparticle film. The nanoparticle film has nanoparticles having an average particle size of equal to or less than about 500 nanometers.

18 Claims, 8 Drawing Sheets

OTHER PUBLICATIONS

Seitz, Oliver et al., "Preparation and characterisation of gold nanparticle assemblies on silanised glass plates;" Elsevier; Colloids and Surfaces A 2003; 218:225-239.

Kim, Beomseok et al., "Self-Organization of Large Gold Nanoparticle Arrays;" J. Am. Chem. Soc. 2001; 123:7955-7956.

"Liquid Waveguide Capillary Cell" product description [online] http://www.wpiine.com/WPI_Web/Spectroscopy/LWCC.html [retrieved Mar. 25, 2004].

Holister, Paul et al. "Nanoparticles, Technology White papers nr.3;" Cientifica Oct. 2003.

Carrabba, Michael M. et al. "Real-Time Hazardous Chemical Emission Rate Monitoring Instrument—Phase II;" Apr. 1996.

* cited by examiner

Film assembled on the surface of Au NP solution a. SERS from NT on gold film
b. SERS from NT on gold NP drop-cast film

CARGO INSPECTION APPARATUS HAVING A NANOPARTICLE FILM AND METHOD OF USE THEREOF

CROSS REFERENCE TO RELATED APPLICATIONS

This application is a continuation-in-part application of U.S. application Ser. No. 10/843,832 entitled "METHOD FOR FORMING NANOPARTICLE FILMS AND APPLICATIONS THEREOF" filed May 12, 2004, which is hereby incorporated by reference in its entirety.

BACKGROUND OF THE INVENTION

Nanoparticles contain hundreds to thousands of single molecules or atoms and have long been recognized as having enhanced chemical and physical properties compared with their bulk forms. Nanoparticles having alloys manufactured from precious metals are of special importance for their catalytic and magnetic properties, useful in information storage media, magnetic refrigeration, audio reproduction and magnetic sealing. Transition metals such as palladium, platinum and cobalt are well known for their catalytic capabilities in bulk and deposited phases. Such alloys can be fabricated through bulk metal processes or through nanoparticle synthesis. It has recently been realized that these nanoparticles with uniformity in size, shape and internal structure could be used as unique building blocks to fabricate nanoparticles-based functional structures by self-assembly. Generally, this nanoparticle-based self-assembly is governed by the nature of the interactions exhibited among the stabilized particles. Various monodisperse nanoparticle materials, including polymers, semiconductors, and metals, have been tested for use in building self-assembly nanoscale devices.

While such nanostructures can be used for manufacturing nanoscale devices, these manufacturing processes are generally expensive and time consuming. In addition, the number of such structures that can be obtained is limited. It is therefore desirable to develop inexpensive and simple methods by which nanoparticle films can be easily generated upon surfaces of solids, and further, it is desirable to use such films for a variety of commercial applications, most notably for the development of analytical techniques that have high sensitivities.

BRIEF DESCRIPTION OF THE INVENTION

Embodiments of the invention disclose a cargo inspection apparatus for the inspection of an analyte carried by a medium. The apparatus includes a housing having an inlet allowing for entry of the medium and an outlet allowing for exit of the medium, and an adsorber disposed within the housing in fluid communication with the medium flow from the inlet to the outlet, the adsorber includes a substrate having disposed thereon a nanoparticle film. The nanoparticle film has nanoparticles having an average particle size of equal to or less than about 500 nanometers.

Further embodiments of the invention disclose a method for detecting an analyte in a cargo hold where the analyte is carried by a medium. The method includes: positioning within the cargo hold an inspection apparatus having a housing with an inlet allowing for entry of the medium and an outlet allowing for exit of the medium, and an adsorber disposed within the housing in fluid communication with the medium flow from the inlet to the outlet, the adsorber including a substrate having disposed thereon a nanoparticle film, the nanoparticle film having nanoparticles with an average particle size of equal to or less than about 500 nanometers; allowing the analyte to be adsorbed at the nanoparticle film, and performing surface enhanced Raman spectroscopy to determine the identity of the analyte.

BRIEF DESCRIPTION OF THE DRAWINGS

Referring to the exemplary drawings wherein like elements are numbered alike in the accompanying Figures.

DETAILED DESCRIPTION OF THE INVENTION

Figure 1:
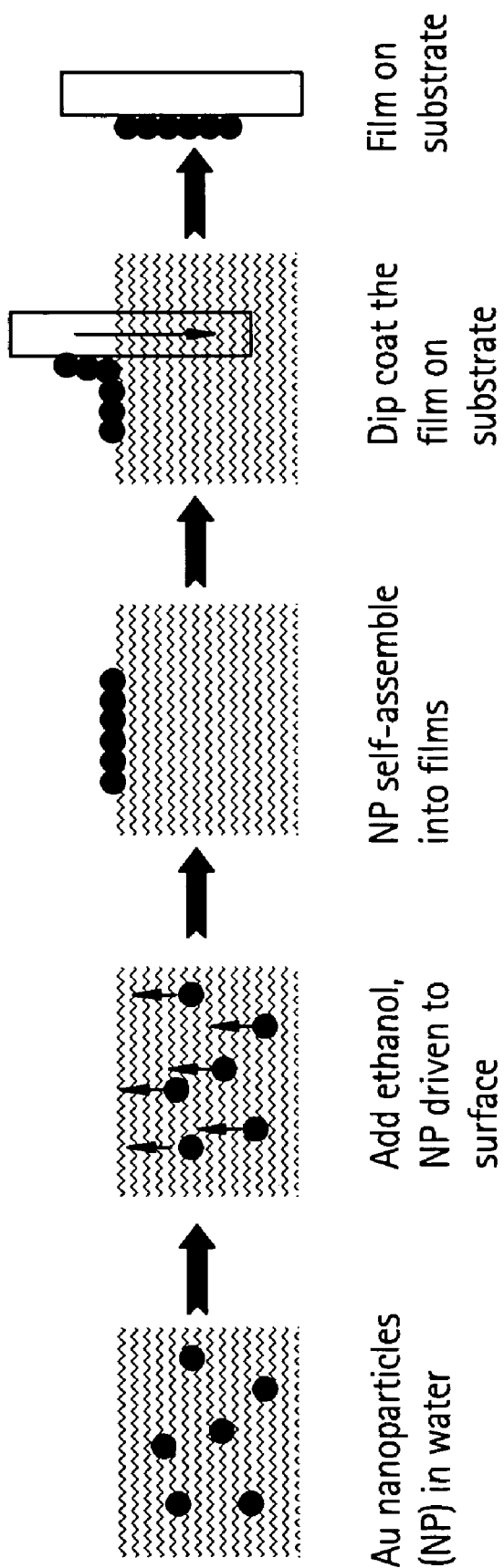
FIG. 1 is a schematic representation of one exemplary embodiment of manufacturing a nanoparticle film.

Disclosed herein is a method for developing nanoparticle films on solid substrates that may be advantageously utilized for analytical techniques, and an apparatus for utilizing such nanoparticle films. A preferred analytical technique for which such films may be used is surface enhanced Raman spectroscopy (SERS). An exemplary embodiment for utilizing such nanoparticle films is a device used for cargo inspection, where the cargo may be exposed to an analyte of interest during transit, and the device may be employed to analyze such analyte using SERS.

The nanoparticles may be either synthesized or purchased commercially. These nanoparticles are then dispersed into a first liquid and exhibit some ability to dissolve in the first liquid. Upon adding at least a second liquid to a solution comprising the first and the second liquid, the nanoparticles spontaneously self-assemble into a porous film at the liquid-gas interface i.e., at the top of the solution. In one embodiment, the gas is air. It is generally desirable for the nanoparticles to have little or preferably no solubility in the second liquid. When a solid substrate is contacted with the solution containing the nanoparticles, the porous film is deposited on the solid substrate. The solid substrate may then be used in surface enhanced Raman spectroscopy and other analytical techniques.

In one embodiment, additional liquids such as a third liquid, a fourth liquid, and so on, may be added to the solution to facilitate the formation of the nanoparticle film. In such a case each liquid may have a dielectric constant that is different from that of the preceding liquids. It is generally desirable for each additional liquid to have a dielectric constant that is different from the liquid containing the nanoparticles.

It is to be noted that the term "solution" as defined herein refers to the total weight of the liquids as well as any nanoparticles that are added to the liquids. It is also to be noted that as used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges disclosed herein are inclusive of the endpoints and independently combinable.

As noted above, the nanoparticle films are first developed on the surface of the solution (i.e., on the top of the solution) and are then transferred to a solid substrate by methods such as dip coating. In one embodiment, the nanoparticles can be completely solid metallic particles or non-metallic particles. In another embodiment, the nanoparticles may comprise a core of a first material, wherein the core is coated with a second material. In another embodiment, the first material can be non-metallic while the second material can be metallic. The nanoparticles may be purchased commercially or manufactured in-situ. Suitable metals from which nanoparticles may be obtained are transition metals, such as, for example, copper, gold, platinum, palladium, aluminum, iron, titanium, vanadium, chromium, nickel, silver, tantalum, tungsten, tin, gallium, germanium, or the like, or a combinations comprising at least one of the foregoing metals. Alloys of the foregoing metals may also be used.

In one embodiment, when the nanoparticles are coated with the second materials, the nanoparticles may comprise a core that comprises a polymer, a ceramic, a metal, or a liquid, or a combination comprising at least one of the foregoing.

The polymers used in the core of the nanoparticle may be thermoplastic polymers, thermosetting polymers, or a combination of thermoplastic polymers with thermosetting polymers. The polymers used in the core of the nanoparticle may be an oligomer, a dendrimer, an ionomer, a homopolymer, a copolymer such as a block copolymer, a graft copolymer, a random copolymer, or the like, or a combination comprising at least one of the foregoing polymers.

Suitable examples of thermoplastic polymers are polyacetals, polyurethanes, polyolefins, polyacrylics, polycarbonates, polystyrenes, polyesters, polyamides, polyamideimides, polyarylates, polyarylsulfones, polyethersulfones, polyphenylene sulfides, polysulfones, polyimides, polyetherimides, polytetrafluoroethylenes, polyetherketones, polyether etherketones, polyether ketone ketones, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polycarboranes, polyoxabicyclononanes, polydibenzofurans, polyphthalides, polyacetals, polyanhydrides, polyvinyl ethers, polyvinyl thioethers, polyvinylalcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, or the like, or combinations comprising at least one of the foregoing thermoplastic polymers.

Suitable examples of thermosetting polymers are epoxies, phenolics, polyesters, polyamides, polyurethanes, polysiloxanes, polybutadienes, polyisoprenes, polyacrylates, polymethacrylates, or the like, or a combination comprising at least one of the foregoing polymers.

Suitable examples of ceramics that may be used in the nanoparticles are silica, alumina, titania, zirconia, ceria, calcium oxide, silicon carbide, silicon nitride, titanium carbide, gallium nitride, or the like, or a combination comprising at least one of the foregoing ceramics.

When the nanoparticles have a core that comprises a polymer or a ceramic, it is desirable to have a metal coating deposited upon the surface of the core. The metal coating may be deposited by chemical vapor deposition, ion implantation, spray painting, or the like. It is generally desirable for the metal coating have a thickness of about 1 to about 500 nanometers (nm). In one embodiment, the metal coating can have a thickness of about 10 to about 400 nm. In another embodiment, the metal coating can have a thickness of about 20 to about 80 nm. In yet another embodiment, the metal coating can have a thickness of about 30 to about 60 nm. A suitable thickness is about 50 nm.

There is no particular limitation to the shape of the nanoparticles, which may be for example, spherical, irregular, plate-like, whiskers, needles, rods, tubes, strands, elongated platelets, lamellar platelets, ellipsoids, micro fibers, nanofibers and nanotubes, elongated fullerenes, or the like, or a combination comprising at least one of the foregoing shapes. The nanoparticles may generally have average largest dimensions of less than or equal to about 500 nanometers (nm). In one embodiment, the particles may have average largest dimensions of less than or equal to about 350 nm. In another embodiment, the nanoparticles may have average largest dimensions of less than or equal to about 200 nm. In yet another embodiment, the nanoparticles may have average largest dimensions of less than or equal to about 75 nm. In yet another embodiment, the nanoparticles may have average largest dimensions of less than or equal to about 50 nm. As stated above, the nanoparticles may generally have average largest dimensions of less than or equal to about 500 nm. In one embodiment, more than 90% of the nanoparticles have average largest dimensions less than or equal to about 500 nm. In another embodiment, more than 95% of the nanoparticles have average largest dimensions less than or equal to about 500 nm. In yet another embodiment, more than 99% of the nanoparticles have average largest dimensions less than or equal to about 500 nm. Bimodal or higher nanoparticle size distributions may be used.

The nanoparticles may generally be present in the solution in an amount of about 0.0000001 wt % to about 20 wt %, based on the total weight of the solution. In one exemplary embodiment, the nanoparticles may generally be present in the solution in an amount of about 0.000001 wt % to about 15 wt %. In another embodiment, the nanoparticles may generally be present in the solution in an amount of about 0.01 wt % to about 1 wt %. In yet another embodiment, the nanoparticles may generally be present in the solution in an amount of about 1 wt % to about 10 wt %. In yet another embodiment, the nanoparticles may generally be present in the solution in an amount of about 10 wt % to about 20 wt %. Exemplary nanoparticles are gold nanoparticles in an amount of about 0.01 wt %, based on the total weight of the solution.

The first liquid has a different dielectric constant from the second liquid. The difference in the dielectric constant between the dielectric constant of the first and the second liquid may be about 1 to about 1000. In one embodiment, the difference in the dielectric constant between the dielectric constant of the first and the second liquid may be about 5 to about 100. In another embodiment, the between the dielectric constant of the first and the second liquid may be about 10 to about 50. An exemplary difference between the first and the second dielectric constant is 56.1.

The first liquid must be capable of dissolving at least a portion of the nanoparticles. In one embodiment, it is generally desirable for the first liquid to dissolve at least about 10 wt % of the nanoparticles. In another embodiment, it is generally desirable for the first liquid to dissolve at least about 20 wt % of the nanoparticles. In another embodiment, it is generally desirable for the first liquid to dissolve at least about 50 wt % of the nanoparticles. In another embodiment, it is generally desirable for the first liquid to dissolve at least about 80 wt % of the nanoparticles. In yet another embodiment, it is generally desirable for the first liquid to dissolve at least about 100 wt % of the nanoparticles.

It is desirable that the second liquid, in addition to having a different dielectric constant from the first liquid, does not solvate the nanoparticles. In other words, it is desirable for the second liquid not to cause the nanoparticles to swell or dissolve in it. It is also desirable for the first liquid and the second liquid to be at least partially miscible in one another. In one embodiment, it is generally desirable for at least 10 wt % of the first liquid to be miscible in the second liquid. In another embodiment, it is generally desirable for at least 20 wt % of the first liquid to be miscible in the second liquid. In yet another embodiment, it is generally desirable for at least 50 wt % of the first liquid to be miscible in the second liquid. In yet another embodiment, it is generally desirable for at least 75 wt % of the first liquid to be miscible in the second liquid. In yet another embodiment, it is generally desirable for at least 100 wt % of the first liquid to be miscible in the second liquid.

While the first liquid and the second liquid cannot be the same, they can both be polar liquids, non-polar liquids, ionic liquids, or combinations comprising at least one of the foregoing liquids, so long as the dielectric constant of the first liquid is different from the second liquid. Generic examples of suitable polar liquids are alcohols, esters, ketones, ethers, amines, thiols, thioesters, sulfides, anisoles, or the like, or a combination comprising at least one of the foregoing polar liquids. Specific examples of suitable polar liquids are water, propylene carbonate, ethylene carbonate, butyrolactone, acetonitrile, benzonitrile, methylene chloride, carbon tetrachloride, nitromethane, nitrobenzene, sulfolane, dimethylformamide, N-methylpyrrolidone, methanol, acetonitrile, nitromethane, ethanol, propanol, isopropanol, butanol, diethyl ether, tetrahydrofuran, or the like, or combinations comprising at least one of the foregoing polar solvents. Examples of suitable non-polar liquids are hydrocarbons such as benzene, toluene, xylene, hexane, cyclohexane, heptane, petroleum ether, paraffin wax, or the like, or combinations comprising at least one of the foregoing non-polar solvents. Co-solvents that comprise combinations of polar liquids, combinations of non-polar liquids and co-solvents comprising at least one aprotic polar liquid and at least one non-polar liquid may also be utilized to modify the swelling power of the first and second liquids.

The first and second liquids may also be ionic liquids if desired. Ionic liquids are organic salts with melting points under 100° C., often even lower than room temperature. Suitable examples of ionic liquids are imidazolium, pyridinium derivatives, phosphonium or tetralkylammonium compounds, or the like, or a combination comprising at least one of the foregoing ionic liquids.

The first liquid may be present in the solution in an amount of about 1 to about 99.99 wt %, based on the total weight of the solution. In one embodiment, the first liquid may be present in the solution in an amount of about 5 to about 80 wt %, based on the total weight of the solution. In another embodiment, the first liquid may be present in the solution in an amount of about 15 to about 60 wt %, based on the total weight of the solution. An exemplary amount of the first liquid in the solution is 80 wt %, based on the total weight of the solution.

The second liquid may be present in the solution in an amount of about 1 to about 99.99 wt %, based on the total weight of the solution. In one embodiment, the second liquid may be present in the solution in an amount of about 20 to about 95 wt %, based on the total weight of the solution. In another embodiment, the second liquid may be present in the solution in an amount of about 40 to about 85 wt %, based on the total weight of the solution. An exemplary amount of the second liquid in the solution is 20 wt %, based on the total weight of the solution.

When the nanoparticles comprise gold, an exemplary first liquid is water in an amount of about 80 wt %, while an exemplary second liquid is ethanol in an amount of about 20 wt %, based on the total weight of the solution.

In one method of making the porous nanoparticle film, the nanoparticles are purchased commercially and dissolved in the first liquid. The dissolution or partial dissolution may occur at room temperature or at temperatures below or above room temperature. In general, a dissolution or partial dissolution temperature of about −100° C. to about 150° C. may be used. In one embodiment, a dissolution or partial dissolution temperature of about −50° C. to about 100° C. may be used. In another embodiment, a dissolution or partial dissolution temperature of about 0° C. to about 50° C. may be used. An exemplary dissolution temperature is about 20 to about 30° C. The second liquid is then added to the vessel containing the first liquid and the nanoparticles. The addition of the second liquid facilitates the migration of the nanoparticles to the surface of the solution. The nanoparticles generally form a monolayer on the surface of the solution. As used herein, the term monolayer refers to a layer of nanoparticles having an overall thickness of generally one nanoparticle thick.

The monolayer may be porous. In one embodiment, the monolayer has a porosity of about 5 to about 90 volume percent (vol. %). In another embodiment, the monolayer has a porosity of about 20 to about 80 vol. %. In yet another embodiment, the monolayer has a porosity of about 40 to about 60 vol. %.

In another method of making the porous nanoparticle film, the nanoparticles are synthesized in a first liquid. In this manner of making the nanoparticles, metal nanoparticles are first synthesized in an aqueous solution (i.e., first liquid) using a standard reduction process. To the first liquid is added a second liquid, which facilitates the migration of the nanoparticles to the surface of the solution. The nanoparticles generally form a monolayer on the surface of the solution. Without being limited by theory, the addition of the second liquid to the first liquid promotes a reduced surface charge on the nanoparticles. The reduced charge decreases the solubility of the nanoparticles in the solution and brings them to the top of the solution. The floating nanoparticles at the top of the solution eventually form porous films at the liquid-gas interface because of strong interactions between the nanoparticles.

After the formation of the nanoparticle film on the surface of the solution, a substrate is introduced into the solution to facilitate the transfer of the film from the liquid-gas interface to the surface of the substrate. The substrate may comprise any known material such as, for example, polymers, ceramics, metals, or the like, or a combination comprising at least one of the foregoing materials. The substrate may have any desired shaped. For example, the substrate may have a surface that is flat, grooved, curved, tubular, braided, patterned, or the like. Suitable examples of substrates are silicon dioxide surfaces (glass), polyethylene, polytetrafluoroethylene, steel, or the like. The substrate may be chosen to modify the properties of the nanoparticle film if desired.

When a tubular surface is immersed into the solution to form a nanoparticle film, it is desirable for the diameter of the tube to be about 1 micrometer to about 7 millimeters. Both, the inner surface as well as the outer surface of the tube may be simultaneously coated.

The substrates may be introduced into the solution at any desirable angle and at any desirable speed. The angle can be in an amount of about 1 to about 180 degrees. In one embodiment, a speed for the immersion of the solid substrate during dip coating is greater than or equal to about 0.1 millimeter per minute (mm/min). In another embodiment, a speed for the immersion of the solid substrate during dip coating is greater than or equal to about 0.5 millimeter per minute (mm/min). In yet another embodiment, a speed for the immersion of the solid substrate during dip coating is greater than or equal to about 1.0 millimeter per minute (mm/min). After removal from the solution, the substrate is dried by exposure to air. It is to be noted that dip coating is only one method by which the film can be removed from the surface. Other methods may also be used to remove the film from the liquid gas interface. For example, the substrate can be used to scoop up the film from its upper surface rather than by immersion of the substrate into the solution.

In one embodiment, the substrate may be immersed into the same solution or into a different solution to form a multilayered film on the surface of the substrate. Special effects may also be created on the substrate by the use of patterned substrates. In addition to the use of patterned substrates, patterns can also be created on substrates by the use of masks during the dip-coating process.

The nanoparticle film may be used for a variety of different applications. It may be used to produce different refractive index coatings on a substrate. It may also be used to produce a glazed surface. The coated substrate may also be used for electronic applications in semi-conductors. As noted above, the nanoparticle film may be advantageously used in analytical techniques such as surface enhanced Raman spectroscopy (SERS). Surface roughness is a very important factor that governs surface-enhanced Raman activity.

The SERS effect leads to a spectacular increase of the Raman scattering cross-section for molecules adsorbed onto suitably roughened surfaces and thus has a large potential in analytical chemistry and for biological applications. This sensitive technique permits the detection of organic molecules adsorbed on rough gold, silver or copper surfaces from very diluted solutions (down to $10^{-9}$ molar (M)), with a maximum enhancement of about $10^{-6}$ to about $10^{-7}$.

Two mechanisms are considered to account for the SERS effect. The electromagnetic mechanism arising from the excitation of localized surface plasmons (LSPs) on roughened features is responsible for the main enhancement due to an enormous increase in the local electric field. The second mechanism is due to an increase in the polarizability of the adsorbed molecule when a resonant charge transfer can occur between the metal and the adsorbate (chemical effect). Thus rough metallic surfaces play an important role in obtaining the SERS effect. For example, excitation of LSP occurs on the metal particles (leading to a huge enhancement of the local electric field), the frequency of which depends on the size, the interparticle distance, and the surrounding medium.

Thus, the present method of depositing the metal nanoparticles on the surface of a substrate can be advantageously used for determining the structure of adsorbed molecules on the metal nanoparticles. This will be demonstrated in the following examples.

The following examples, which are meant to be exemplary, not limiting, illustrate methods of manufacturing some of the various embodiments of the nanoparticle films and also demonstrate how these films may be used in various analytical applications.

EXAMPLES

Example 1

This example was conducted to demonstrate that a gold nanoparticle film can be deposited on a glass substrate from a solution. The glass substrate was not treated with a coupling agent prior to the deposition of the nanoparticle film from the solution. FIG. 1 is a schematic showing how the gold nanoparticles may be deposited onto the glass substrate.

2 to 5 milliliters (mL) of 38.8 millimolar (mM) sodium citrate was rapidly added to 95 mL of 1 mM tetrachloroauric acid ($AuHCl_4$) aqueous solution, which was brought to boil with vigorous stirring. Boiling was continued for 10 minutes and then the heat was removed and stirring was continued for an additional 15 minutes. The resulting gold nanoparticle sizes were about 15 nm to about 50 nm as determined by transmission electron microscopy.

After the formation of the gold nanoparticles, ethanol in an amount of 25 grams was added to the solution. As shown in the FIG. 1, the addition of the second liquid promotes the migration of the gold nanoparticles to the surface.

A glass substrate is then immersed into the solution to yield a nanoparticle film on the surface of the glass.

Figure 2:
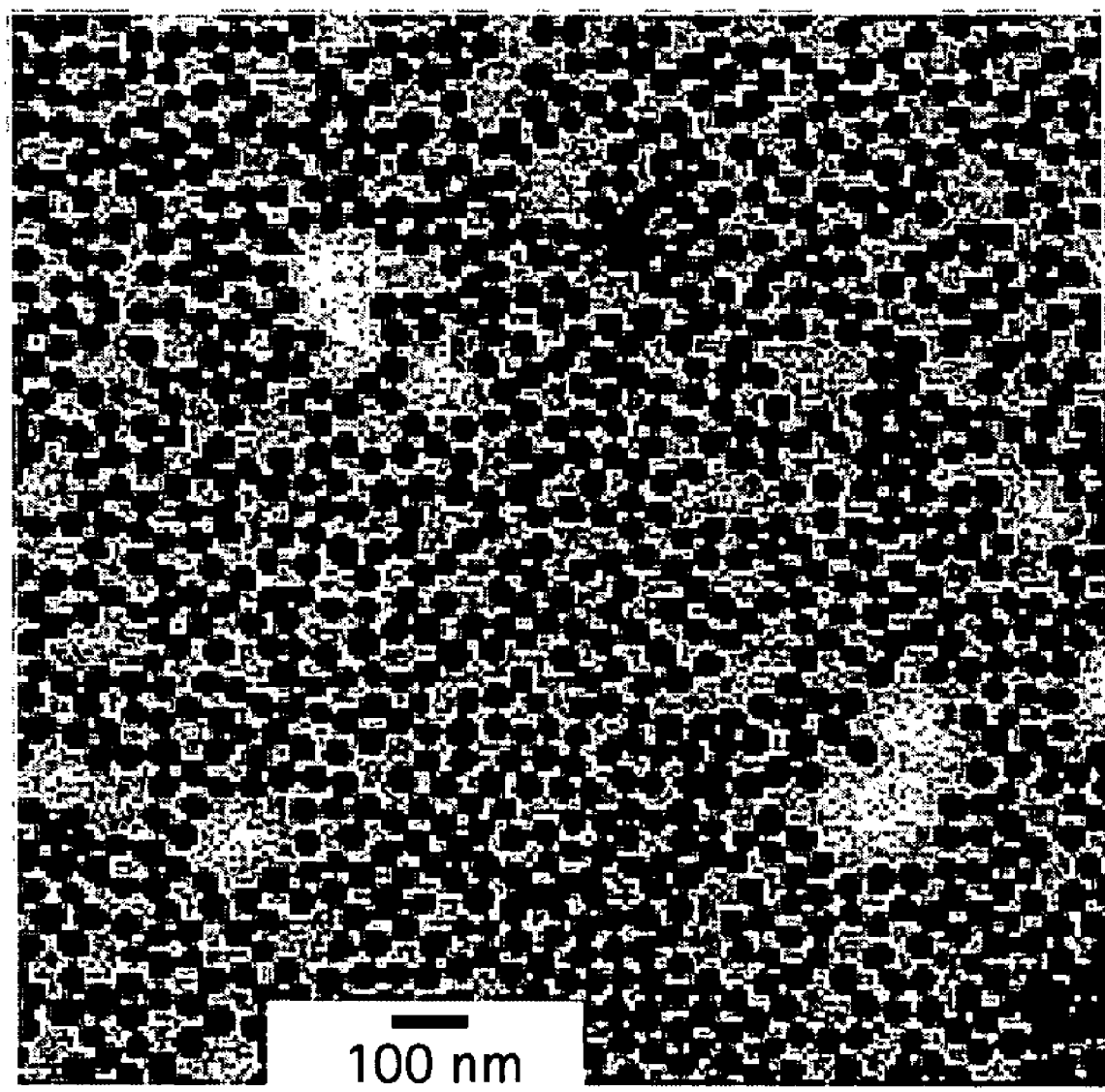
FIG. 2 is a transmission electron micrograph of a gold nanoparticle film assembled on the surface of the solution.

FIG. 2 shows a transmission electron micrograph of a film of gold nanoparticles formed on the surface of the solution. The film was lifted from the surface of the solution using a copper grid and was then examined in the transmission electron microscope. From the FIG. 2, it may be seen that the gold nanoparticles form a porous film.

Example 2

Figure 3:
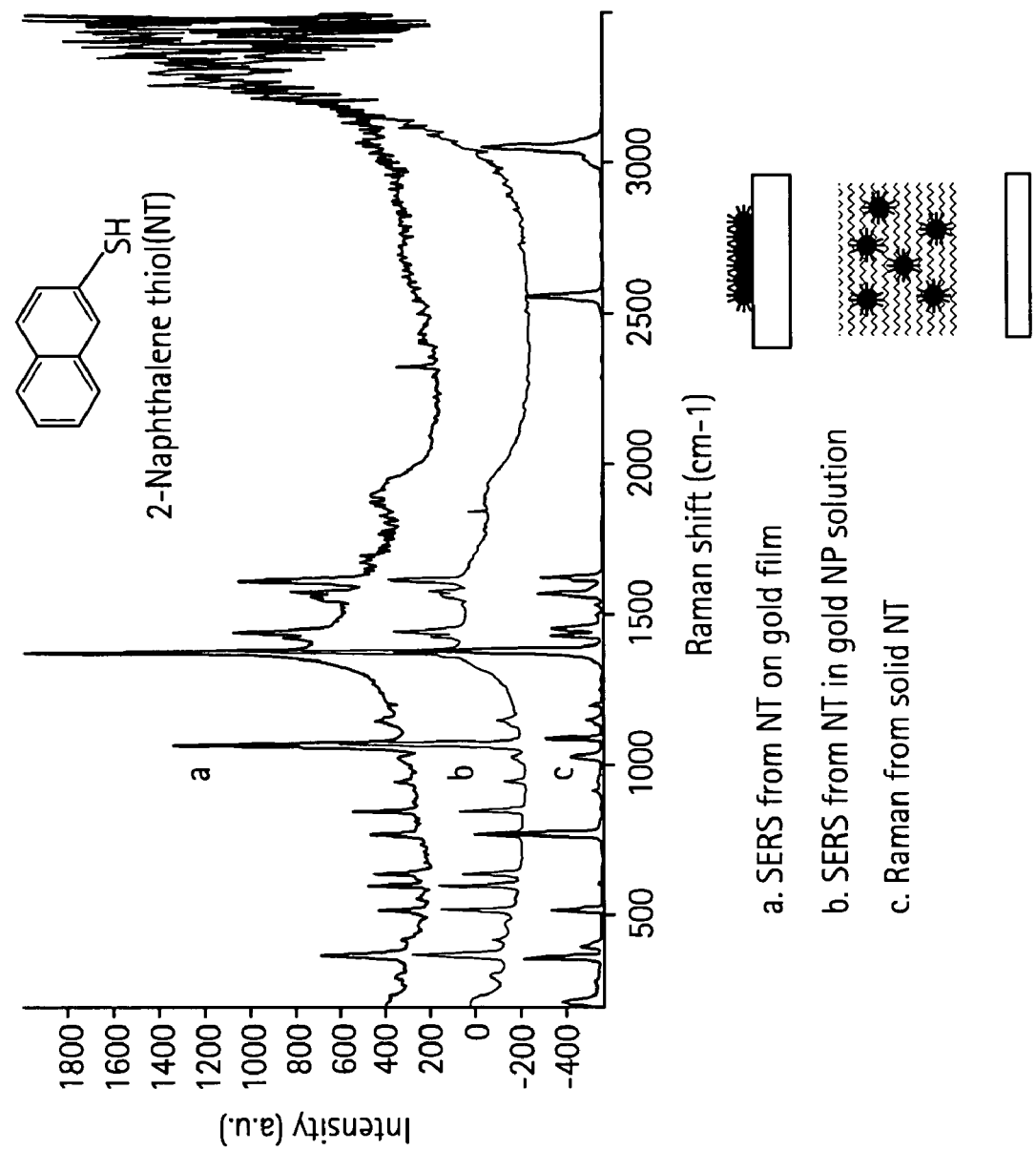
FIG. 3 depicts spectra obtained from (a) surface enhanced Raman spectroscopy (SERS) performed on 2-Naphthalene thiol deposited on a gold nanoparticle film deposited on the surface of a solid substrate (b) SERS performed on 2-Naphthalene thiol deposited into a solution of gold nanoparticles (0.1 mg/ml) in water. (c) Raman spectroscopy on a solid 2-Naphthalene thiol slab.

This example was undertaken to demonstrate the sensitivity of SERS when 2-Napthelene thiol (NT) (2.5 micromolar (uM) in ethanol) was deposited on the surface of the gold nanoparticle film present on a glass substrate. Raman spectroscopy was performed by using a laser wavelength of 785 nanometers. The laser power was 27 milliwatts (mW) and the data collection time was 1 minute. The SERS response from the glass substrate is indicated by the letter (a)

in the FIG. 3. The SERS response from a gold solution may be seen as indicated by the letter (b) in FIG. 3. The SERS response from the film can be comparable with the response from the solution. The response from these samples is compared against the comparative sample (c) when the SERS is performed on a slab of the NT itself. From the spectra shown in the FIG. 3, it may be seen that the SERS signal from 2.5 um 2-Naphthelene thiol is comparable with the Raman signal from a solid slab thereby indicating that SERS performed on the gold nanoparticle film gives greater resolution and sensitivity than when it is performed directly on the material of interest.

Figure 4:
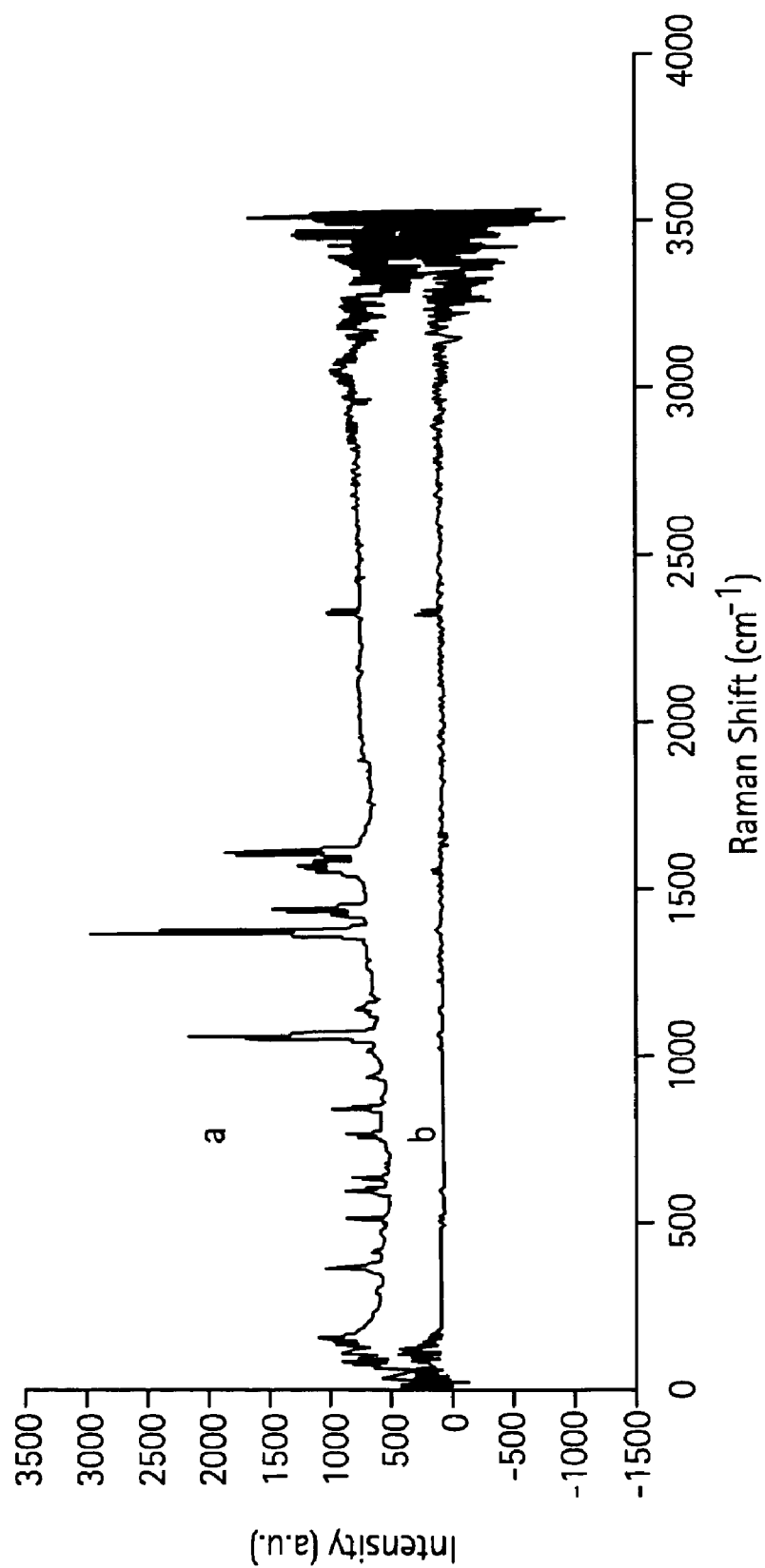
FIG. 4 depicts spectra obtained from (a) surface enhanced Raman spectroscopy (SERS) performed on 2-Naphthalene thiol deposited on a gold nanoparticle film deposited on the surface of a solid substrate (b) SERS performed on 2-Naphthalene thiol deposited on a gold nanoparticle drop-cast film deposited on the surface of a solid substrate.

Similarly, FIG. 4 shows the difference between SERS spectra that was obtained from NT deposited on gold film (a) and spectra that was obtained from NT on gold NP drop-cast film (b). The drop cast sample was made from the same gold solution that was used for preparing the gold film. The solution was directly deposited on the glass slide and the solvent was allowed to dry to obtain the drop-cast sample. The SERS signal is much stronger in the gold nanoparticle film than in the drop cast sample, from which there is barely any SERS signal.

Example 3

Figure 5:
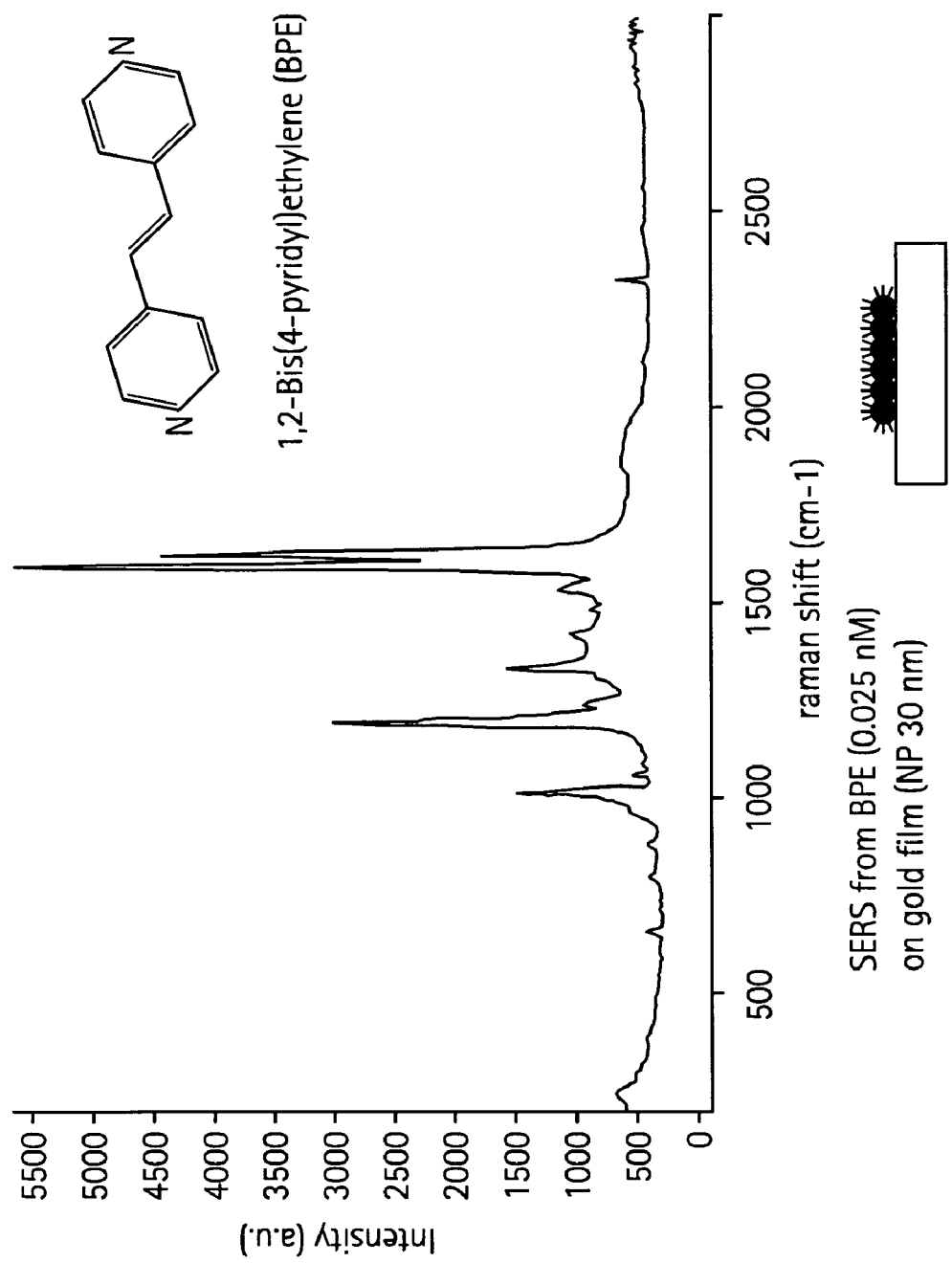
FIG. 5 depicts spectra obtained from surface enhanced Raman spectroscopy (SERS) performed on 1,2-Bis(4-pyridyl)ethylene (BPE) deposited on a gold nanoparticle film deposited on the surface of a solid substrate.

This example was undertaken to demonstrate SERS spectra obtained from 1,2-Bis(4-pyridyl)ethylene (BPE) deposited upon gold nanoparticle film. The gold nanoparticles were 30 nm in size. The BPE concentration was 0.025 mM in ethanol. As may be seen in the spectra in FIG. 5, the ability of SERS to detect the BPE is clearly enhanced by the presence of BPE on the gold nanoparticles.

Example 4

Figure 6:
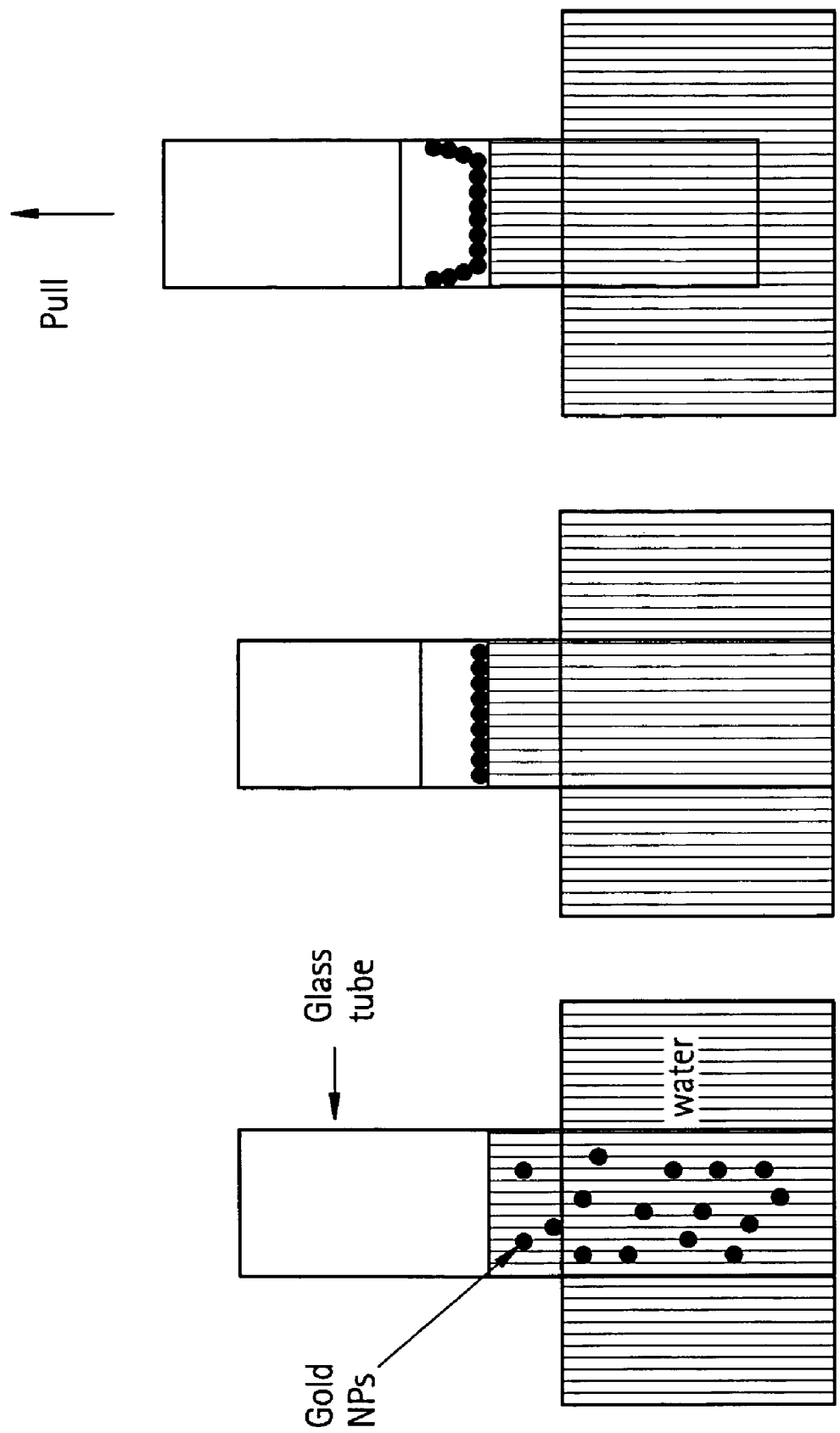
FIG. 6 depicts one exemplary method of forming a nanoparticle film on the inner surface of a tube.
Figure 7:
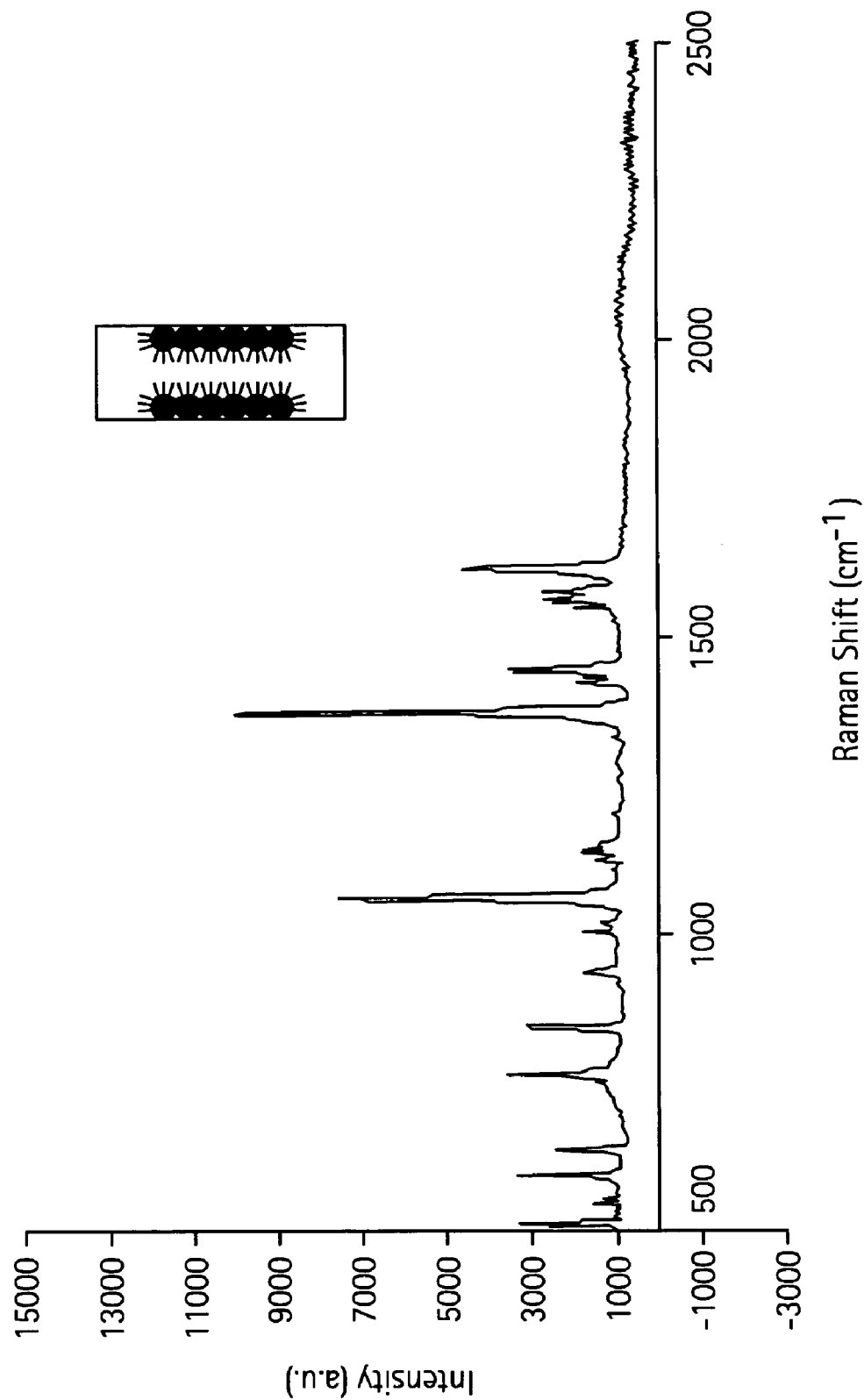
FIG. 7 depicts spectra obtained by performing surface enhanced Raman spectroscopy (SERS) on the inner surface of a tube.

This example demonstrates one method for the formation of a nanoparticle film on the inside of a tube and the detection of an analyte that is deposited upon the nanoparticles on the film. In this example, as shown in FIG. 6, a tube of a desired internal diameter is partially immersed into a solution containing gold nanoparticles. The gold nanoparticles form a film on the inner surface of the tube when the tube is withdrawn from the solution. An analyte is then deposited on the inside of the tube. The molecules of the analyte are supported on the surface of the gold nanoparticles as shown in FIG. 7. FIG. 7 shows a spectra obtained when SERS was performed on the inside of the tube.

From the aforementioned examples it may be seen that the use of a metal nanoparticle film can be advantageously used for the detection of trace amounts of unknown analytes. This technique can be advantageously used to detect concentrations in the part per million regime ($10^{-6}$). In one embodiment, this technique can be advantageously used to detect concentrations in the parts per billion regime ($10^{-9}$).

Figure 8:
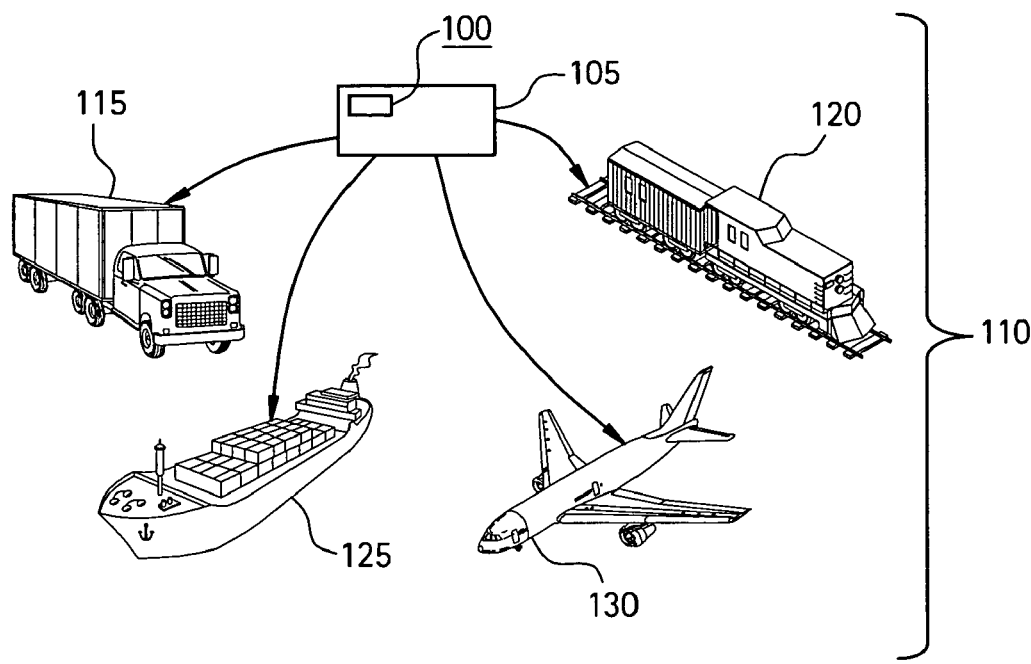
FIG. 8 depicts the use of a cargo inspection apparatus in accordance with embodiments of the invention.
Figure 9:
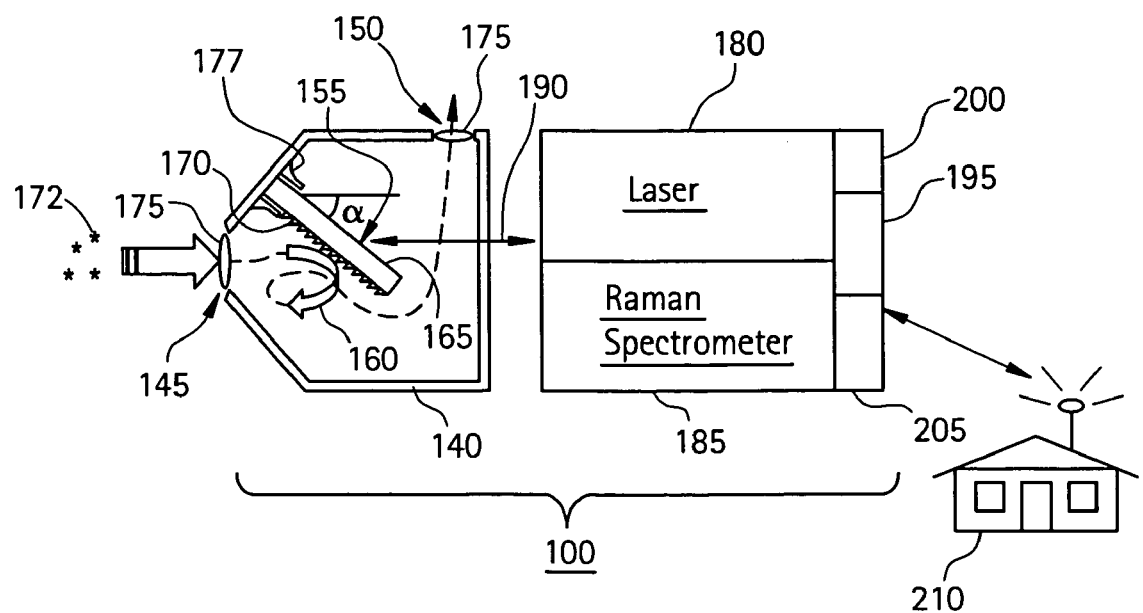
FIG. 9 depicts a cargo inspection apparatus in accordance with embodiments of the invention.

Referring now to FIGS. 8 and 9, a cargo inspection apparatus 100 for the inspection of an analyte utilizing embodiments of the aforementioned nanoparticle film is depicted. FIG. 8 depicts apparatus 100 disposed within a cargo hold 105 of a transporter 110, such as a truck 115, a railroad train 120, an ocean going vessel 125, or an airplane 130, for example, and FIG. 9 depicts a more detailed view of apparatus 100, which may be placed at any convenient location within cargo hold 105, but is preferably located in an area exposed to free or forced convection air flow.

In an embodiment, apparatus 100 includes a housing 140 having an inlet 145 that allows for entry of an analyte-carrying-medium, such as air, and an outlet 150 that allows for exit of the medium. Inlet 145 and outlet 150 may be distinct and separate openings, or may be a single opening serving both functions. Disposed within housing 140 is an adsorber 155, which is in fluid communication with the medium flow, generally depicted at 160, from inlet 145 to outlet 150. Adsorber 155 includes a substrate 165 having disposed on a surface thereof a nanoparticle film 170, made in accordance with aforementioned methods, which may be formed of nanoparticles having an average particle size of equal to or less than about 500 nanometers (nm). In an alternative embodiment, the nanoparticles of nanoparticle film 170 have an average particle size of about 50 nm. As discussed previously, the nanoparticles of nanoparticle film 170 may be a metal or a core material coated with a metal, where the metal may be copper, gold, platinum, palladium, aluminum, iron, titanium, vanadium, chromium, nickel, silver, tantalum, tungsten, tin, gallium, germanium, or a combination having at least one of the foregoing metals. In an embodiment, the metal is gold. Nanoparticle film 170 may be a monolayer of nanoparticles, or may be made from multiple layers of nanoparticles, in accordance with aforementioned methods.

To improve the adsorption of an analyte 172 at nanoparticle film 170, both of which being depicted in an exaggerated form, adsorber 155 may be oriented at an angle α relative to the direction of medium flow 160 at inlet 145, with nanoparticle film 170 being oriented toward inlet 145 for better exposure to incoming analytes. Angle α is chosen so as to cause air turbulence in the vicinity of nanoparticle film 170, thereby increasing the interaction time between air flow 160 and nanoparticle film 170. Since airborne analytes may be present in a solution of the analyte in a concentration of less than or equal to about the part per million regime ($10^{-6}$), or even in a concentration of less than or equal to about the part per billion regime ($10^{-9}$), and may be of a particle size equal to or less than an order of magnitude of about $10^2$ micrometers, a filtration membrane 175 may be disposed at inlet 145 to better discriminate between analytes of interest and particles of lesser or no interest. In an embodiment, filtration membrane 175 may be at inlet 145, at outlet 150, or at both.

Housing 140 and adsorber 155 may be an integral unit, or adsorber 155 may be a replaceable cartridge that is removably connected to housing 140 at supports 177. Where adsorber 155 is a replaceable cartridge, housing 140 may reusable.

In alternative embodiments, apparatus 100 may serve as a sample gathering device or as an on-board real-time analysis device. Where apparatus 100 serves as a sample gathering device, apparatus 100 is placed in cargo hold 105 of transporter 110 at the beginning of a journey, and removed at the end of the journey. At the end of the journey, apparatus 100 is subjected to testing where surface enhanced Raman spectroscopy (SERS) is performed on nanoparticle film 170 to determine the identity of any adsorbed analytes. In an embodiment, adsorber 155 may be removed from apparatus 100 for SERS testing.

In an embodiment where apparatus 100 serves as an on-board real-time analysis device, apparatus 100 includes a laser 180 and a Raman spectrometer 185, each of which being arranged in signal communication with nanoparticle film 170 via fiber optics, lenses and mirrors, depicted generally at 190. During the transportation of cargo holder 105, nanoparticle film 170 is subjected to SERS testing, with the temporal data relating to analyte adsorption being analyzed, processed and stored by an on-board computer 195, thereby providing an inspector at the conclusion of the journey with a chronology of when and where exposure to a particular analyte may have occurred. A power supply 200 may be included with apparatus 100 for powering laser 180, Raman spectrometer 185 and computer 195. In an alternative embodiment, a wireless communicator 205 is in signal communication with computer 195 for sending temporal data to a centralized station 210 for real-time monitoring of sensitive cargo.

In view of the foregoing, a method for detecting an analyte in cargo hold 105 may be accomplished by positioning inspection apparatus 100 in cargo hold 105, allowing nanoparticle film 170 to be exposed to an analyte-carrying medium and to adsorb the analyte thereof, and then performing SERS on nanoparticle film 170 to determine the identify of the analyte.

As disclosed, some embodiments of the invention may include some of the following advantages: a cost effective inspection apparatus having a reusable housing and a replaceable adsorber cartridge; the ability to cost effectively test for the presence of an analyte over the duration of transportation of a cargo; the ability to easily convert a SERS inspection apparatus from a sample gathering device to an on-board real-time analysis device; and, the ability to cost effectively test for the presence of an analyte that may be present only in a small concentration and a small physical size.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cargo inspection apparatus for the inspection of an analyte carried by a medium, the apparatus comprising:
   a housing having an inlet allowing for entry of the medium and an outlet allowing for exit of the medium; and
   an adsorber disposed within the housing in fluid communication with the medium flow from the inlet to the outlet, the adsorber comprising a substrate having disposed thereon a nanoparticle film;
   wherein the nanoparticle film comprises nanoparticles having an average particle size of equal to or less than about 500 nanometers.

2. The apparatus of claim 1, wherein the nanoparticles have an average particle size of about 50 nanometers.

3. The apparatus of claim 1, wherein the nanoparticles comprise a metal.

4. The apparatus of claim 3, wherein the metal is copper, gold, platinum, palladium, aluminum, iron, titanium, vanadium, chromium, nickel, silver, tantalum, tungsten, tin, gallium, germanium, or a combination comprising at least one of the foregoing metals.

5. The apparatus of claim 3, wherein the metal comprises gold.

6. The apparatus of claim 1, wherein the nanoparticle film is a monolayer.

7. The apparatus of claim 1, wherein the adsorber is oriented at an angle relative to the direction of medium flow at the inlet, the nanoparticle film being oriented toward the inlet.

8. The apparatus of claim 1, wherein the medium comprises air.

9. The apparatus of claim 1, further comprising a filtration membrane disposed at the inlet, at the outlet, or at both the inlet and the outlet, the filtration membrane being discriminative of particles entering the housing having a particle size equal to or greater than an order of magnitude of about $10^2$ micrometers.

10. The apparatus of claim 1, wherein the nanoparticle film is made from the method comprising:
    dispersing nanoparticles in a first liquid;
    adding a second liquid to the first liquid to form a nanoparticle film on top of a solution comprising the first liquid, the second liquid and the nanoparticles, wherein the second liquid has a dielectric constant that is different from a dielectric constant of the first liquid; and
    contacting the substrate with the solution to deposit the nanoparticle film onto the contacted portion of the substrate.

11. The apparatus of claim 10, wherein:
    the nanoparticles comprise gold;
    the first liquid comprises water;
    the second liquid comprises ethanol; and
    the substrate comprises silica.

12. The apparatus of claim 1, further comprising:
    a laser and a raman spectrometer each in signal communication with the nanoparticle film allowing for real time inspection of the analyte.

13. The apparatus of claim 1, wherein the adsorber is removably connected to the housing.

14. A method for detecting an analyte in a cargo hold, the analyte being carried by a medium, the method comprising:
    positioning within the cargo hold an inspection apparatus comprising a housing having an inlet allowing for entry of the medium and an outlet allowing for exit of the medium, and an adsorber disposed within the housing in fluid communication with the medium flow from the inlet to the outlet, the adsorber comprising a substrate having disposed thereon a nanoparticle film, the nanoparticle film comprising nanoparticles having an average particle size of equal to or less than about 500 nanometers;
    allowing for the adsorption of the analyte at the nanoparticle film; and
    performing surface enhanced Raman spectroscopy to determine the identity of the analyte.

15. The method of claim 14, wherein:
    the substrate comprises silica; and
    the nanoparticles comprise gold.

16. The method of claim 15, wherein the nanoparticles have an average particle size of equal to or less than about 50 nanometers.

17. The method of claim 14, wherein:
    the surface enhanced Raman spectroscopy is detectably responsive to the presence of the analyte in a solution of the analyte in a concentration of less than or equal to about the part per million regime ($10^{-6}$).

18. The method of claim 14, wherein:
    the surface enhanced Raman spectroscopy is detectably responsive to the presence of the analyte in a solution of the analyte in a concentration of less than or equal to about the part per billion regime ($10^{-9}$).

* * * * *